United States Patent [19]

Shinoda

[11] Patent Number: 5,679,837

[45] Date of Patent: Oct. 21, 1997

US005679837A

[54] PROCESS FOR PRODUCING ACETIC ACID OR METHYL ACETATE AND CATALYST THEREFOR

[75] Inventor: Sumio Shinoda, Tokyo, Japan

[73] Assignee: Daicel Chemical Industries, Ltd., Tokyo, Japan

[21] Appl. No.: 604,797

[22] Filed: Feb. 23, 1996

Related U.S. Application Data

[60] Division of Ser. No. 238,175, May 4, 1994, which is a continuation-in-part of Ser. No. 204,343, Mar. 9, 1994, Pat. No. 5,393,919.

[30] Foreign Application Priority Data

Aug. 19, 1993 [JP] Japan .................................. 5-205066

[51] Int. Cl.$^6$ .................................................. C07C 67/00
[52] U.S. Cl. ................................................ 560/239; 562/538
[58] Field of Search ............................. 562/538; 560/239

[56] References Cited

PUBLICATIONS

Chemical Abstract Plus 1991:45423, Shinoda et al, J Chem Soc., Chem.Commun. (1990), 21, 1511–12, 1991.

*Primary Examiner*—Samuel Barts
*Attorney, Agent, or Firm*—Flynn, Thiel, Boutell & Tanis, P.C.

[57] ABSTRACT

The present invention relates to:

(1) a novel catalyst which has a high catalytic activity, is useful in the production of acetic acid and/or methyl acetate from methanol, and is obtained through ion exchange of an anion of an anion exchanger with an anion of an Ru—Sn hetero-polynuclear compound;

(2) a novel catalyst which has a high catalytic activity, is useful in the production of acetic acid and/or methyl acetate from methanol, and is obtained through ion exchange of a cation of a cation exchanger with a Ru complex and treatment with a Sn compound;

(3) a process for producing acetic acid and/or methyl acetate from methanol through a one-stage reaction in a gas phase wherein the catalytic activity is maintained throughout the reaction; and (4) a process for producing acetic acid and/or methyl acetate in the presence of a highly active catalyst, for example, the catalyst specified in (1) or (2), at a high reaction rate.

2 Claims, 3 Drawing Sheets

PROCESS FOR PRODUCING ACETIC ACID OR METHYL ACETATE AND CATALYST THEREFOR

This is a division of Ser. No. 08/238,175, filed May 4, 1994, which is a CIP of Ser. No. 08/204,343, filed March 9, 1994 now U.S. Pat. No. 5,393,919.

BACKGROUND OF THE INVENTION

1. Field of the Invention

The present invention relates to a catalyst which is useful in the production of acetic acid and/or methyl acetate from methanol, a process for producing this catalyst and a process for producing acetic acid and/or methyl acetate from methanol as a starting material with this catalyst in a gas phase.

2. Description of the Related Art

Acetic acid has been industrially produced in a large amount by the methanol carbonylation method, i.e., so-called Monsanto's method. In this method, methanol is reacted with carbon monoxide in a liquid phase in the presence of a catalytic system containing a rhodium component and an iodide.

However, it is necessary in these methods to use rhodium which is highly expensive. Further, an ancillary facility is necessary in order to obtain carbon monoxide of high purity, and a location condition for a factory is restricted in some cases. Furthermore, there is a problem that methyl iodide, which is used as an iodide, corrodes the apparatus. In addition, since the above-mentioned reaction is usually effected in a liquid phase system containing water, the recovery of the acetic acid thus formed requires much energy.

Meanwhile, there has been proposed the use of an Ru—Sn heteronuclear cluster (a polynuclear compound) containing an anion comprising $[Ru(SnCl_3)_5L]^{3-}$ (wherein L represents a ligand) as a catalyst for producing acetic acid and methyl acetate from methanol through a one-stage reaction in a liquid phase [Sumio Shinoda and Tetsu Yamakawa, "One-step Formation of Methyl Acetate with Methanol used as the Sole Source and Catalysis by $Ru^{II}$—$Sn^{II}$ Cluster Complexes", J. Chem. Soc., Chem. Commun., p.p. 1511–1512 (1990)]. Further, it is also reported that the Ru (II)—Sn (II) cluster complex represented by $[Ru(SnCl_3)_6]^{4-}$ is useful in a gas phase/solid phase reaction for producing acetic acid and methyl acetate from methanol by a one-stage reaction [Sumio Shinoda, Appl. Catal. 92A, L1–L5 (1992)].

However, the above-mentioned heteronuclear clusters have a solubility in methanol as small as about 0.05 mM. In addition, since the above heteronuclear cluster is an anionic complex, the solubility of the above heteronuclear clusters is smaller not only in the acetic acid formed but also in common organic solvents. Thus, it is impossible to elevate the concentration of the catalyst, and therefore, the reaction rate also can not be enhanced. Furthermore, it is sometimes observed that formaldehyde is formed by the dehydrogenation of methanol and the metal contained in the catalyst is reduced and precipitated by the formaldehyde, which causes the deactivation of the catalyst within a short period of time. In particular, the catalyst is liable to be deactivated when reacted at a high temperature.

Accordingly, it is an object of the present invention to provide a novel catalyst which has a high catalytic activity and is useful for producing acetic acid and/or methyl acetate from methanol, that is, a novel catalyst capable of producing acetic acid and/or methyl acetate from methanol as a single source by a one-stage reaction at a high selectivity while maintaining a high catalytic activity for a long period of time.

It is another object of the present invention to provide a process for producing the catalyst described above.

It is another object of the present invention to provide a process for producing acetic acid and/or methyl acetate from methanol through a one-stage reaction in a gas phase wherein the catalytic activity can be maintained at a high level throughout the reaction time.

It is another object of the present invention to provide a process for producing acetic acid and/or methyl acetate in the presence of a highly active catalyst at a high reaction rate at a high selectivity.

DISCLOSURE OF THE INVENTION

Summary of the Invention

The present inventor has extensively studied for achieving the above-mentioned objects. As the result, he has found that these objects can be achieved by reacting methanol in a gas phase with the use of a solid catalyst and that a specific catalyst with the use of an anion exchanger exhibits a high catalytic activity in a gas phase reaction wherein methanol is used as a starting material. The present inventor has further found that methylal or methyl formate can be produced by a gas phase reaction wherein methanol is used as a starting material and a solid catalyst is employed. Thus, the present invention has been completed based on these findings.

Thus, the present invention provides a catalyst (A) prepared by exchanging an anion of an anion exchanger with an anion of an Ru—Sn hetero-polynuclear compound represented by the following general formula (1):

$$[Ru(SnX_3)_m(Y)_n]\cdot Z \qquad (1)$$

[wherein X represents a halogen atom, an alkyl group, a cycloalkyl group, an aryl group, an aralkyl group or an alkoxyl group; Y represents a ligand; m is an integer of 1 to 6, n is an integer of 0 to 5 and m+n is an integer of 1 to 6; and Z represents a counter cation].

It is preferable that the above-mentioned Ru—Sn heteropolynuclear compound is the one represented by the general formula (1) wherein X is a halogen atom, Y is $PR^a_3$ or $R^bCN$ (wherein $R^a$ represents an alkyl group, a cycloalkyl group, an aryl group, an aralkyl group, an alkoxyl group, an aryloxy group or an arylalkoxyl group; and $R^b$ represents an alkyl group, a cycloalkyl group, an aryl group or an aralkyl group), m+n is 6 and n is 0 or 1.

The present invention further provides a process for producing acetic acid and/or methyl acetate characterized by dehydrogenation methanol in a gas phase in the presence of a solid catalyst.

Furthermore, the present invention provides a process for producing methylal or methyl formate characterized by using methanol as a starting material and effecting a as phase reaction in the presence of a solid catalyst.

In addition, further investigations with respect to the Ru—Sn catalyst described above, i.e., the catalyst (A), were made by the present inventor in order to achieve the objects described above. As the result, he has found that a solid catalyst (B) wherein a cation of a cation exchanger is subjected to a cation exchange with a Ru complex and a Sn component is supported shows a high catalytic activity and completed the present invention.

Thus, the present invention relates to a catalyst (B) for preparing acetic acid and/or methyl acetate, which comprises a cation exchanger, a ruthenium complex containing ruthenium of a positive valence which is supported on the cation exchanger by a cation exchange and a tin compound of zero valence, divalence or tetravalence which is supported on the above cation exchanger, and a process For producing acetic acid and/or methyl acetate, in which methanol is reacted in the presence of the catalyst (B).

The catalyst (B) can be produced by subjecting a cation of a cation exchanger to a cation exchange with a complex containing ruthenium of a positive valence and processing the cation exchanger described above with a tin compound of a divalence or tetravalence.

The present inventor reported a process for preparing acetic acid and/or methyl acetate using a catalyst comprising a cation exchanger and a Ru—Sn complex ["One-step formation of acetic acid (methyl acetate) with methanol used as the sole source by heterogeneous catalysts derived from supported Ru(II)—Sn(II) heteronuclear clusters", by Tetsu Yamakawa and Sumio Shinoda, ABSTRACT OF THE 4TH JAPAN-KOREA SYMPOSIUM ON CATALYSIS, CATALYSIS SOCCIETY OF JAPAN, p.p. 99–100, May 17, 1993; A printed article, by Sumio Shinoda and Tetsu Yamakawa, titled "One-step formation reaction (3) of acetic acid (methyl acetate) with methanol used as the sole source by Ru(II)—Sn(II) heteronuclear cluster catalyst in liquid phase homogeneous system or solid/liquid phases heterogeneous system, on pages 7 and 8, and delivered on Jun. 24, 1993, by POLYMER SOCIETY at symposium for chemical use of carbon sources; and Article by Sumio Shinoda, titled "One-step formation reaction of acetic acid with methanol used as the sole source based on the multi-functinal catalystic action of Ru(II)—Sn(II) heteronuclear cluster catalyst in homogeneous system or heterogeneous system, delivered by Junior-members of CATALYST SOCIETY on Aug. 6, 1993].

The scope and application of the present invention will become apparent from the following detailed description. However, it should be understood that the detailed description and examples, while indicating preferred embodiments of the invention, are given by way of illustration only, since various changes and modifications within the spirit and scope of the present invention will become apparent to those skilled in the art from this detailed description.

Though the present invention will be described in detail hereinafter, the scope of the present invention is not restricted by the following description.

The process according to the present invention is characterized in that acetic acid and/or methyl acetate or methylal and/or methyl formate are produced by a gas phase reaction by using methanol as a starting material.

DETAILED DESCRIPTION OF THE INVENTION

Now, the catalyst (A) according to the present invention will be described.

The gas phase reaction is effected in the presence of a solid catalyst. As the solid catalyst, a heteronuclear cluster (a polynuclear compound) of Ru(II)—Sn(II) is preferable. In order to elevate the catalytic activity, it is particularly preferable to use a complex represented by the following general formula (1) as the Ru—Sn hetero-polynuclear compound.

$$[Ru(SnX_3)_m(Y)_n] \cdot Z \qquad (1)$$

[wherein X represents a halogen atom, an alkyl group, a cycloalkyl group, an aryl group, an aralkyl group or an alkoxyl group; Y represents a ligand; m is an integer of 1 to 6, n is an integer of 0 to 5 and m+n is an integer of 1 to 6; and Z represents a counter cation].

As the Ru—Sn hetero-polynuclear compound, it is preferable to use, among them, a complex represented by the general formula (1) wherein X is a halogen atom. Y is $PR^a_3$ or $R^bCN$ (wherein $R^a$ represents an alkyl group, a cycloalkyl group, an aryl group, an aralkyl group, an alkoxyl group, an aryloxy group or an arylalkoxyl group; and $R^b$ represents an alkyl group, a cycloalkyl group, an aryl group or an aralkyl group), m+n is 6 and n is 0 or 1.

Examples of the halogen atom represented by X in the above general formula (1) include a fluorine atom, a chlorine atom, a bromine atom and an iodine atom. As a preferable halogen atom, a chlorine atom may be cited.

Alternately, X may represents an alkyl group, a cycloalkyl group, an aryl group, an aralkyl group or an alkoxyl group.

Examples of the ligand represented by Y in the above general formula (1) include a halogen atom, a hydrogen atom, a coordinative carbon-containing ligand, a coordinative nitrogen-containing ligand, a coordinative oxygen-containing ligand, a coordinative phosphorus-containing ligand, a coordinative sulfur-containing ligand and a coordinative arsenic-containing ligand.

Now the ligand will be described more definitely.

The halogen atom as the ligand is the same as that represented by X. As a preferable halogen atom, a chlorine atom may be cited.

Examples of the "coordinative carbon-containing ligand" as used in the present invention include alkyl groups, cycloalkyl groups, aryl groups, aralkyl groups, monovalent cyclic dienyl groups such as a cyclopentadienyl group and a cyclooctadienyl group which may be substituted, olefins which may be substituted, CO and RNC (wherein R represents an alkyl group, a cycloalkyl group, an aryl group, an aralkyl group or an alkoxyl group).

Examples of the "coordinative nitrogen-containing ligand" as used in the present invention include $NH_3$, amines (for example, amines such as methylamine, ethylamine, dimethylamine and diethylamine, diamines such as ethylenediamine, nitrogen-containing heterocyclic compounds such as imidazole, pyridine, pyrimidine, piperidine, piperazine, morpholine and phenanthroline and nitrogen-containing aromatic compounds such as aniline) and compounds represented by $R^bCN$ (wherein $R^b$ represents an alkyl group, a cycloalkyl group, an aryl group, an aralkyl group or an alkoxyl group). Among these ligands, $NH_3$ is preferable.

Examples of the "coordinative oxygen-containing ligand" as used in the present inveniton include $H_2O$, alcohols including aliphatic alcohols and aromatic alcohols, ethers including aliphatic ethers and aromatic ethers, a hydroxyl ion and alkoxide ions.

Examples of the "coordinative phosphorus-containing ligand" as used in the present invention include $PR^a_3$ or $O=PR^a_3$ (wherein $R^a$ represents an alkyl group, a cycloalkyl group, an aryl group, an aralkyl group, an alkoxyl group, an aryloxy group or an arylalkoxyl group) and bis(diphenylphosphino)alkanes such as 1,2-bis (diphenylphosphino)ethane (dppe), 1,3-bis (diphenylphosphino)propane (dppp) and 1,4-bis (diphenylphosphino)butane (dppb), i.e., bidentate phosphine ligands. Since the bis(diphenylphosphino)alkanes have bidentate coordination characteristics, L represents ½{bis (diphenylphosphino)alkane}.

Examples of the "coordinative sulfur-containing ligand" as used in the present invention include a thioalkoxide ion and compounds represented by RSR and RSH (wherein R represents an alkyl group., a cycloalkyl group, an aryl group, an aralkyl group or an alkoxyl group).

Examples of the "coordinative arsenic-containing ligand" as used in the present invention include compounds represented by $AsR_3$ or $O=AsR_3$ (wherein R represents an alkyl group, a cycloalkyl group, an aryl group, an aralkyl group or an alkoxyl group) and bidentate arsine ligands such as 1,2-bis(diphenylarsino)ethane. Since the 1,2-bis (diphenylarsino)ethane has bidentate coordination characteristics, L represents ½{1,2-bis(diphenylarsino)ethane}.

Examples of the alkyl groups given in the description of X and Y in the above general formula (1) include a methyl group, an ethyl group, a n-propyl group, an isopropyl group, a n-butyl group, an isobutyl group, a pentyl group and a hexyl group.

Examples of the cycloalkyl groups include a cyclopentyl group, a cyclohexyl group and a cyclooctyl group. The aryl groups include a phenyl group, a naphthyl group and the like. The aralkyl groups include a benzyl group, a phenylethyl group, a benzhydryl group and the like.

Examples of the alkoxyl groups include alkoxyl groups corresponding to the above-mentioned alkyl groups, for example, a methoxy group, an ethoxy group, a n-propoxy group, an isopropoxy group, a n-butoxy group, an isobutoxy group, a pentyloxy group and a hexyloxy group.

In the description of Y in the above general formula (1), examples of the aryloxy groups include a phenoxy group and a naphthoxy group, while examples of the arylalkoxyl groups include a phenylmethoxy group, a phenylethoxy and a phenylpropoxy group.

Examples of the counter cation represented by Z in the above-mentioned general formula (1) include a proton; alkali metal ions such as a lithium ion, a potassium ion and a sodium ion; alkaline earth metal ions such as a calcium ion and a barium ion; and cations represented by the general formula: $XaH_4^+$, $XaH_3R^+$, $XaH_2R_2^+$, $XaHR_3^+$ or $XaR_4^+$ (wherein Xa represents N, P or As and R represents an alkyl group, a hydroxyalkyl group or an aryl group).

Examples of the alkyl group R in the above general formula representing the counter cation include linear and branched alkyl groups carrying about 1 to 4 carbon atoms such as a methyl group, an ethyl group and a propyl group. Examples of the hydroxyalkyl group include lower hydroxy alkyl groups carrying about 1 to 4 carbon atoms such as a hydroxymethyl group, a 2-hydroxyethyl group, a 2-hydroxypropyl group and a 3-hydroxypropyl group. Examples of the aryl group include a phenyl group.

As particular examples of the cation represented by the above-mentioned general formula, for example, quaternary ammonium ions such as an ammonium ion, a tetramethylammonium ion, a tetraethylammonium ion and a tetrapropylammonium ion; and quaternary phosphonium ions such as a phosphonium ion, a tetramethylphosphonium ion, a tetraethylphosphonium ion, a tetrahydroxymethylphosphonium ion and a tetraphenylphosphonium ion may be cited.

Among the complexes represented by the above general formula (1), the compounds represented by the general formula (1) wherein X is a halogen atom, Y is $PR^a_3$ or $R^bCN$ (wherein $R^a$ represents an alkyl group, a cycloalkyl group, an aryl group, an aralkyl group, an alkoxyl group, an aryloxy group or an arylalkoxyl group; and $R^b$ represents an alkyl group, a cycloalkyl group, an aryl group or an aralkyl group), m+n is 6 and n is 0 or 1 are preferable.

More particularly, the complexes represented by the above general formula (1) include those represented by the following general formulae (1a), (1b) and (1c):

[Ru(SnX₃)₆]·Z     (1a)

[Ru(SnX₃)₅(PR^a₃)]·Z     (1b)

[Ru(SnX₃)₅(R^bCN)]·Z     (1c)

[wherein X represents a halogen atom, an alkyl group, a cycloalkyl group, an aryl group, an aralkyl group or an alkoxyl group; $R^a$ represents an alkyl group, a cycloalkyl group, an aryl group, an aralkyl group, an alkoxyl group, an aryloxy group or an arylalkoxyl group; $R^b$ represents an alkyl group, a cycloalkyl group, an aryl group or an aralkyl group; and Z represents a counter cation].

Preferable examples of the substituent $R^a$ in the compound represented by the general formula (1b) include aryl groups such as a phenyl group.

Preferable examples of the substituent $R^b$ in the compound represented by the general formula (1c) include alkyl groups carrying 1 to 3 carbon atoms, in particular, a methyl group.

The above-mentioned solid catalyst can be prepared by the conventional techniques such as precipitation, impregnation and ion exchange.

The complex represented by the above general formula (1a) can be prepared, for example, in accordance with a method described in J. Chem. Soc., Dalton Trans., 2329 (1984). More particularly, it may be prepared by, for example, mixing a ruthenium halide, a tin halide and an acid such as hydrochloric acid, sulfuric acid and nitric acid, adding a solution of a compound corresponding to the counter cation Z thereto, collecting the precipitate thus formed and washing and drying the same. The completion of the reaction between the ruthenium halide and the tin halide can be judged depending on a change in the color of the solution.

The complex represented by the general formula (1c) can be prepared by mixing a complex represented by the formula [RuX(SnX₃)₅]·Z (wherein X and Z are as defined above) with a solution of a compound corresponding to $R^bCN$ (wherein $R^b$ is as defined above), adding, for example, AgBF₄ to he obtained reaction mixture, collecting the precipitate thus formed and washing and drying the same [see Can. J. Chem., 60, 1304 (1982)].

Further, the complex represented by the general formula (1b) can be prepared by mixing a complex represented by the general formula (1c) with a solution of an organophosphorus compound corresponding to $PR^a_3$ (wherein $R^a_3$ is as defined above) at a temperature of, for example, around 50° to 80° C., collecting the precipitate thus formed and washing and drying the same. By this reaction, $R^bCN$ in the complex represented by the general formula (1c) is replaced by the organophosphorus compound to thereby give the complex represented by the general formula (1b).

The Ru—Sn hetero-polynuclear compound may be subjected to he reaction as a solid catalys as such. However, it is preferable to use said compound in a state supported on a support so as to further elevate the catalytic activity.

Examples of the support include inorganic supports such as activated carbon, silica, alumina, silica-alumina, clay minerals, e.g., zeolite, copper oxide, bentonite, magnesia, silica-magnesia, titania and zirconia; and organic ones such as ion exchange resins and chelating resins. Among these supports, one comprising at least one member selected from the group consisting of inorganic supports such as activated carbon, silica, alumina, zeolite, copper oxide, titania and zirconia; and organic ones such as ion exchange resins and chelating resins is preferable. Preferable examples of the support include those which are resistant to high temperatures exceeding the reaction temperature.

The present invention is advantageous in that a support having a catalytic ability can be used. Examples of the support having a catalytic ability include those containing copper oxide. As the copper oxide, CuO and $Cu_2O$ may be cited. Divalent copper oxide CuO may be cited as a preferable copper oxide.

The support having a catalytic ability may be a composite oxide system containing other metal oxide(s), in addition to the above copper oxide. Examples of the other oxides include various oxides, for example, oxides of elements of the group VIa in the periodic table (for example, $Cr_2O_3$, $CrO_3$ and $Mo_2O_3$) and oxides of elements of the group IIb in the periodic table (for example, ZnO and CdO). Examples of preferable composite oxides include those consisting of copper oxide and chromium oxide, e.g., $CuO$—$Cr_2O_3$ and $CuO$—$CrO_3$ and those consisting of copper oxide and zinc oxide, e.g., $CuO$—$ZnO$.

As still preferable examples of the support, those wherein at least copper oxide, preferably the above-mentioned composite oxide, is supported on an inorganic support such as silica as cited above may be cited. When such a support is used, it is possible to extremely elevate (for example about 10- to 100-fold) the catalytic activity of the complex represented by the above general formula (1), though the support per se has little catalytic activity.

A support containing copper oxide can be prepared in accordance with, for example, methods described in Japanese Patent Publication-A Nos. 68716/1978 and 108916/1978. That is to say, it can be prepared by impregnating a support with a solution of, for example, copper sulfate, copper nitrate, copper carbonate or copper acetate, followed by drying or baking. A support containing a composite oxide can be prepared by mixing the above-mentioned copper salt solution with a solution of, for example, sulfate, nitrate, acetate or carbonate of other metal(s) such as chromium and zinc and impregnating a support therewith, followed by baking.

A complex can be supported on a support by depositing a solution of the complex represented by the general formula (1) on the support or impregnating the support with said solution, or kneading a solution of the complex represented by the general formula (1) with the support, and drying the obtained mixture.

The amount of the catalyst to be supported can be selected over a wide range, so long as the efficiency for producing acetic acid and methyl acetate is not lowered thereby. For example, from 0.1 to 200 parts by weight, preferably from 1 to 100 parts by weight and still preferably from 5 to 80 parts by weight, of the catalyst may be used based on 100 parts by weight of the support.

A solid catalyst may be in any of the forms including powder, granule, pellet, bar, ellipsoid and sphere.

The above-mentioned Ru—Sn hetero-polynuclear compound is an anion complex. Thus, the solid catalyst may be the one obtained through ion exchange between an anion of an anion exchanger and an anion of an Ru—Sn hetero-polynuclear compound [in particular, a complex represented by the above-mentioned general formula (1)]. A compound obtained through ion exchange between an anion of an anion exchanger and an anion of a complex represented by the above-mentioned general formula (1) can be represented by the following general formula (3):

$$[Ru(SnX_3)_m(Y)_n] \cdot I \qquad (3)$$

[wherein I represents an anion exchanger; and X, Y, m and n are as defined above].

Such compounds, in particular, those represented by the general formula (3) are advantageous in having a higher catalytic activity than a solid catalyst carried on the above-mentioned support.

As the anion exchanger, for example, inorganic anion exchangers such as zirconium hydroxide, water-containing titania [for example, a compound represented by the compositional formula $TiO_2 \cdot zH_2O$ (wherein z represents a number not less than 0)], water-containing zirconia [for example, a compound represented by the compositional formula $ZrO_2 \cdot zH_2O$ (wherein z represents a number not less than 0)] and layered ion-exchangeable compounds; and anion exchange resins may be cited. Preferable examples of the anion exchanger include inorganic ion exchangers, in particular, hydrotalcite and hydrocalumite which are two dimensional layered compounds having an intercalated anion capable of undergoing ion exchange.

A compound obtained through ion exchange with an inorganic anion exchanger is advantageous in a long catalytic life which is seemingly caused by the pairing of the anion of the Ru—Sn hetero-polynuclear compound with the inorganic counter cation. Particularly, the effect can be achieved highly when an inorganic layered compound is used as an anion exchanger.

The above-mentioned hydrotalcite involves a series of compounds represented by a compositional formula (2) consisting of a brucite layer $[(Ma^{2+})_{2x}(Mb^{3+})_2(OH^-)_{4x+4}]^{2+}$, which is a positively charged hydroxide layer, an intercalated anion $[A^{y-}]_{2/y}$, and intercalated water:

$$[(Ma^{2+})_{2x}(Mb^{3+})_2(OH^-)_{4x+4}]^{2+} \cdot [A^{y-}]_{2/y} \cdot zH_2O \qquad (2)$$

[wherein $Ma^{2+}$ represents a divalent metal ion; $Mb^{3+}$ represents a trivalent metal ion; $A^{y-}$ represents a y-valent anion; x and y are natural numbers; and z represents a number not less than 0].

Examples of the above-mentioned divalent metal ion $Ma^{2+}$ include a magnesium ion, a nickel ion and a zinc ion. Examples of the trivalent metal ion $Mb^{3+}$ include an aluminum ion, a chromium ion and an iron ion.

In the above compositional formula (2), x is usually an integer of from 2 to 5 and y is 1 or 2. Examples of the above-mentioned anion $A^{y-}$ include inorganic ions such as a carbonate ion, a sulfate ion and halogen ions, e.g., a chloride ion; and organic anions such as a terephthalate ion.

The ion exchange of an anion exchanger with the above-mentioned Ru—Sn hetero-polynuclear compound can be effected by the conventional ion exchange techniques.

When hydrotalcite is used as an anion exchanger and subjected to ion exchange by using a complex represented by the general formula (1) as the above-mentioned hetero-polynuclear compound, a solid catalyst wherein the intercalated anion $A^{y-}$ of hydrotalcite has been ion-exchanged with an anion represented by the formula $[Ru(SnX_3)_m(Y)_n]$ [wherein X, Y, m and n are as defined above] can be obtained.

Next, the catalyst (B) of the present invention will be described.

The kind of he cation exchanger in the catalyst of the present invention is not specifically limited as long as it has a cation exchange ability. There are exemplified as the cation exchanger, for example, an inorganic cation exchanger such as a natural or synthetic zeolite, a coal exchanger including a sulfonated coal, a heat-resistant ion exchanger of a zirconium phosphate series, and montmorillonite: and an organic cation exchanger such as a strong-acidic cation exchange resin including a polystyrenesulfonic acid type resin having a sulfone group or a sulfonylmethyl group and a weak-acidic cation exchange resin having a carboxyl group, a phenolic hydroxyl group or a phosphone group.

Included in the preferred cation exchanger are the inorganic cation exchanger and the strong-acidic cation exchange resin, particularly the cation exchanger having thermal stability at temperatures higher than a reaction temperature (for example, an inorganic cation exchanger having high thermal stability, such as zeolite).

There are exemplified as zeolite having the structure of condensed aluminosilicate, for example, A type zeolite, X type zeolite, Y type zeolite, ZSM-5 type zeolite, ZSM-11 type zeolite, ZSM-34 type zeolite, T type zeolite, faujasite, mordenite, erionite, chabazite and ferrierite. These zeolites can be used alone or in combination of two or more kinds.

A Si/Al ratio in zeolite can suitably be selected and Si/Al resides in the range of, for example, 1 to 10,000, preferably 1 to 50. A cation in zeolite is not specifically limited and includes $Li^+$, $K^+$, $Na^+$, $Cs^+$, $Rb^+$, $NH_4^+$, and $Ca^{2+}$. Zeolite containing $Na^+$ such as NaY type zeolite is used as zeolite in many cases.

The specific surface area of the cation exchanger such as an inorganic cation exchanger is not specifically limited and a BET specific surface area resides in the range of, for example, 20 to 3000 $m^2/g$. The cation exchanger having the specific surface area in the range of from 100 to 2000 $m^2/g$ is extensively used.

Ru in a ruthenium complex (Ru complex) supported by a cation exchange is preferably divalent or trivalent. The cation represented by the general formula (13) is included in the cation of the Ru complex:

$$[Ru(L)_m]^{q+} \quad (13)$$

wherein L represents wherein L represents a halogen atom, a hydrogen atom, or a ligand selected from the group consisting of a coordinative carbon-containing ligand, a coordinative nitrogen-containing ligand, a coordinative oxygen-containing ligand, a coordinative phosphorus-containing ligand, a coordinative sulfur-containing ligand, a coordinative arsenic-containing ligand, and a coordinative atom contained in a cation exchanger; m represents an integer of 0 to 6 and q represents an integer of 1 to 3; provided that when m is 2 or more, a plurality of L each may be the same or different from one another.

In the above formula (13), the halogen atom and the ligands have the same meanings as those described with respect to catalyst (A).

A coordinative atom contained in the cation exchanger includes, for example, $O^{2-}$ which is a latice oxygen in zeolite.

A preferred Ru complex includes a complex wherein L represents $NH_3$, Cl, Br, CO, $N_2$ or $H_2O$ and m is 6.

Preferred cation of the Ru complex introduced into the cation exchanger includes, for example, $[Ru(NH_3)_6]^{q+}$, $[Ru(NH_3)_5Cl]^{q+}$, $[Ru(NH_3)_5(CO)]^{q+}$, $[Ru(NH_3)_5(N_2)]^{q+}$, and $[Ru(NH_3)_5H_2O]^{q+}$ (in which q is 1 to 3).

The amount of the Ru complex for use resides in the range of, for example, 0.1 to 25% by weight, preferably 0.5 to 10% by weight in terms of Ru atom, i.e., when the amount of the Ru complex is determined as the amount of Ru atom, based on the ion exchanger.

As described above, the tin compound is further supported on the cation exchanger which was subjected to a cation exchange. A divalent or tetravalent tin compound is preferred as the tin compound. The divalent tin compound includes, for example, stannous halide (stannous fluoride, stannous chloride, stannous bromide, and stannous iodide) and tin alkoxide (for example, tin dimethoxide, tin diethoxide, tin dipropoxide, and tin dibutoxide). The tetravalent tin compound includes, for example, stannic halides (stannic fluoride, stannic chloride and stannic bromide). Of these divalent or tetravalent tin compounds, stannous halides, particularly stannous chloride is extensively used. The amount of the tin compound supported resides in the range of, for example, 1 to 5000 weight parts, preferably 5 to 1000 weight parts per 100 weight parts of Ru in the Ru complex described above. In the present invention, Ru has a positive valence of, for example, one to four. Sn in the formula (11) and the formula (14) described later has a valence of zero, two or four.

In the case where the Ru complex is a Ru complex containing divalent or trivalent Ru in the formula (13) described above, a complex containing divalent Ru can be formed by reducing the complex containing trivalent Ru, and a complex containing trivalent Ru can be formed by introducing the complex containing trivalent Ru by a cation exchange or oxidizing the complex containing divalent Ru. Trivalent Ru (III) seems to be reduced to divalent Ru (II) during a reaction process. The catalyst of the present invention includes as well such a catalyst that contains the divalent Ru (II) complex formed during the reaction process.

Further, as an example of a supported state of the tin compound, $SnZ_3^-$ (in which Z represents a halogen atom or an alkoxy group) which elevates a catalyst activity is coordinated to Ru (II) or Ru (III) in the formula (13) described above, which is obtained by eliminating a part or all of L (for example, $NH_3$) in the formula (13), and a Ru (II)—Sn (II) cluster catalyst and a Ru (III)—Sn (II) cluster catalyst seem to be present in a mixture.

Such a complex can be represented by, for example, the following general formula (14):

$$[Ru(L)_n(SnZ_3)_r] \quad (14)$$

wherein L represents a halogen atom, a hydrogen atom, or a ligand selected from the group consisting of a coordinative carbon-containing ligand, a coordinative nitrogen-containing ligand, a coordinative oxygen-containing ligand, a coordinative phosphorus-containing ligand, a coordinative sulfur-containing ligand, a coordinative arsenic-containing ligand, and a coordinative atom contained in the cation exchanger; Z represents a halogen atom, an alkyl group, a cycloalkyl group, an aryl group, an aralkyl group, or an alkoxy group; L may be bridged between Ru and Ru and/or Ru and Sn; n represents an integer o 0 to 5 and r represents an integer of 1 to 6, in which n+r is 1 to 6; provided that when n is 2 or more, a plurality of L each may be either the same or different from one another.

The complex in which $SnZ_3^-$ is coordinated may be a cation, a nonion or an anion. The halogen atom represented by Z includes fluorine, chlorine, bromine and iodine. The preferred halogen atom is the chlorine or bromine atom, particularly the chlorine atom. The alkoxy group represented by Z includes, for example, methoxy, ethoxy, propoxy, isopropoxy, butoxy, isobutoxy and t-butoxy.

The catalyst (B) of the present invention can be represented by, for example, the following general formula (11):

$$[Ru(L)_n(SnZ_3)_r] \cdot I \quad (11)$$

wherein L represents a halogen atom, a hydrogen atom, or a ligand selected from a group consisting of a coordinative carbon-containing ligand, a coordinative nitrogen-containing ligand, a coordinative oxygen-containing ligand, a coordinative phosphorus-containing ligand, a coordinative sulfur-containing ligand, a coordinative arsenic-containing ligand, and a coordinative atom contained in a cation exchanger; Z represents a halogen atom, an alkyl group, a cycloalkyl group, an aryl group, an aralkyl group or an alkoxy group; L may be bridged between Ru and Ru and/or Ru and Sn; I represents a cation exchanger; n represents an integer of 0 to 5 and r represents an integer of 1 to 6, in which n+r is 1 to 6, provided that when n is 2 or more, a plurality of L each may be either the same or different from one another.

The catalyst may be of any of powder, granule, pellet, stick, ellipse, and sphere.

Since in the catalyst (B) of the present invention, a Ru—Sn cluster is trapped in a cage of the cation exchanger, it has a characteristic that the catalyst life is very long as compared with that of the catalysts supported on other supports (for example, copper oxide, activated carbon, hydrotalcite and silica). It is supposed that this is due to that a catalyst component is trapped in the cage of the ion exchanger and deactivation thereof by coagulation is suppressed. In addition, a co-catalyst effect attributable to a Sn component is markedly revealed and thus a catalytic activity is very high.

To obtain a catalyst in which a Ru—Sn complex, which is an anion (or a nonion or a cation) and has a large molecular size, is trapped in the cage of a cation exchanger, a method which comprises cation-exchanging of a cation exchanger with a Ru complex cation and treating the cation exchanger thus obtained with a tin compound can be effected more easily than a method which comprises isolating a Ru—Sn cluster once and then introducing it into a cation exchanger.

Of the compounds represented by the above formula (13), the salt of a complex (complex salt) containing Ru can be used as the Ru complex described above. The Ru complex salt can be represented, for example, by the following general formula (12):

$$[Ru(L')_m]^{q+} \cdot A^{q-} \quad (12)$$

wherein L' represents a halogen atom, a hydrogen atom, or a ligand selected from the group consisting of a coordinative carbon-containing ligand, a coordinative nitrogen-containing ligand, a coordinative oxygen-containing ligand, a coordinative phosphorus-containing ligand, a coordinative sulfur-containing ligand, and a coordinative arsenic-containing ligand; A represents an anion; m represents an integer of 0 to 6 and q represents an integer of 1 to 3; provided that when m is 2 or more, a plurality of L' each may be either the same or different.

The anion represented by A includes, for example, inorganic anions such as a halide ion including fluoride, chloride, bromide and iodide, sulfate ion and phosphate ion; and organic anions such as an organic carboxylate anion including acetate, trichloroacetate and trifluoroacetate and a sulfonate anion including methanesulfonate, ethanesulfonate, benzenesulfonate and p-toluenesulfonate. Of these anions, preferred in many cases is inorganic anions, particularly halide ions, for example, a chloride ion.

The ion exchange can be carried out by a conventional method, for example, by mixing the ion exchanger described above with a solution of the Ru complex described above. There are used as the solution of the above Ru complex in many cases, an aqueous solution and an aqueous solution of an inorganic acid such as hydrogen halide corresponding to the above halide ion (for example, hydrochloric acid), nitric acid, sulfuric acid and phosphoric acid, or an organic acid corresponding to the organic anion described above. The solution of the Ru complex salt described above has pH residing in the range of, for example, 2 to 6 according to the kinds of the complex salt and the ion exchanger.

The ion exchange can be carried out, for example, in the range of 10° to 40° C. A stirring time resides in the range of, for example, 10 minutes to 96 hours, and stirring is carried out for 1 to 48 hours in many cases.

After finishing a cation exchange, the ion exchanger is treated with the tin compound exemplified above. The treatment with the tin compound can be carried out by dipping the ion exchanger, which has been subjected to the cation exchange with the Ru complex, in the solution of the tin compound, or mixing the ion exchanger with the solution of the tin compound. The tin compound can be used in the form of an aqueous solution, an aqueous solution of an inorganic acid such as a hydrogen halide (for example, hydrochloric acid), nitric acid, sulfuric acid and phosphoric acid, or a solution of an organic solvent such as alcohol, e.g. methanol and ethanol, and others. Further, a stannous halide may be used in the form of a solution containing a salt such as sodium chloride and potassium chloride, if necessary.

Dipping or mixing of the ion exchanger on which the Ru complex is supported by the cation exchange can be carried out at a suitable temperature, for example, at 10° to 40° C. A dipping or stirring time is not specifically limited and resides, for example, 10 minutes to 96 hours and 1 to 60 hours in many cases.

These operations can be carried out in air or an inert atmosphere of nitrogen, helium or argon under an atmospheric pressure, a reduced pressure or an applied pressure. After supporting the tin compound on the cation exchanger, the cation exchanger separated by a method such as filtration can be washed and dried according to necessity to thereby obtain a catalyst. The catalyst may be granulated or molded by a conventional method using a binder according to necessity.

Moreover, the process for producing acetic acid and/or methyl acetate will be described.

In the process of he present invention, methanol can be reacted as well in a liquid phase in the presence of the solid catalyst (A) or (B) described above, but a gas phase/solid phase reaction in which methanol is contacted with the catalyst in a gas phase is advantageously utilized. When methanol is contacted with such a solid catalyst (A) or (B) in a gas phase, acetic acid and/or methyl acetate is formed by a one-stage reaction. It is conceivable that this reaction proceeds as follows:

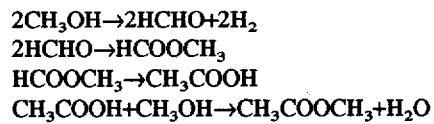

$2CH_3OH \rightarrow 2HCHO + 2H_2$ $2HCHO \rightarrow HCOOCH_3$ $HCOOCH_3 \rightarrow CH_3COOH$ $CH_3COOH + CH_3OH \rightarrow CH_3COOCH_3 + H_2O$ As these reaction formulae clearly show, the acetic acid thus formed further reacts with the methanol employed as the starting material to thereby give methyl acetate. Therefore, the formation of methyl acetate can be suppressed and acetic acid can be formed at a high efficiency by lowering the ratio of the methanol in the reaction system.

Further, as apparent from the above reaction formulae, in the process of the present invention, acetic acid and/or methyl acetate can be formed by the use of formaldehyde (or a formaldehyde source such as paraformaldehyde) or methyl formate as a starting material. Although, therefore, acetic acid and/or methyl acetate can be formed by using at least one material selected from the group consisting of methanol, formaldehyde and methyl formate, it is advantageous to use inexpensive methanol.

Under some reaction conditions, methyl formate and methylal, which are useful as precursors of acetic acid and methyl acetate, are formed as by-products in a relatively large amount. Accordingly, the process of the present invention is usable also as a process for producing methyl formate and/or methylal by appropriately selecting the reaction conditions.

Dehydrogenation of methanol in a gas phase can be effected at a temperature of, for example, from 50° to 400° C., preferably from about 100° to 300° C. This reaction is preferably effected in an inert gas (for example nitrogen gas, helium gas or argon gas) atmosphere under atmospheric or elevated pressure. The reaction may be carried out by any of the batchwise and continuous processes.

When the reaction is to be carried out batchwise, the ratio of methanol to the complex may be appropriately selected within such a range as not to lower the efficiency of the formation of acetic acid and methyl acetate. The ratio of methanol per mol of the complex is, for example, from 0.1 to 10,000 mol, preferably from about 10 to 1,000 mol.

A preferable method for dehydrogenating methanol in a gas phase includes one wherein gaseous methanol is continuously supplied to the solid catalyst. In such a continuous process, the feed rate of methanol per mol of the complex can be selected within such a wide range as not to lower the efficiency of the formation of acetic acid and methyl acetate, for example, from 0.001 to 1,000 mol/min, preferably from about 0.01 to 100 mol/min.

In the case of a continuous process, any of the conventional processes, for example, the flow-through reaction system wherein gaseous methanol is supplied to a bed packed with a solid catalyst, the reaction system wherein a solid catalyst is suspended in gaseous methanol to thereby form a fluidized bed, or the reaction distillation system is usable. Among the continuous methods, the flow-through reaction system is preferable. A reaction product can be treated in a refining process such as distillation according to necessity to give acetic acid and/or methyl acetate.

When catalyst (B) is employed in the continuous process, a space velocity W/F can be selected in a wide range, where a supplying rate of methanol per a unit catalyst weight is represented in terms of mole/hr, and W/F resides in the range of, for example, 0.001 to 10,000 (g-cata.h mol$^{-1}$), preferably 0.01 to 5,000 (g-cata.h mol$^{-1}$).

The catalyst (B) of the present invention shows a specific behavior that increasing a space velocity notably improves a selectivity of acetic acid and/or methyl acetate and can control the composition of a reaction product. That is, methyl formate and acetic acid or methyl acetate are formed at the space velocity of from 50 to 300 (g-cata.h mol$^{-1}$). Methyl formate is scarcely formed at the space velocity of from 500 to 10,000 (g-cata.h mol$^{-1}$), particularly 1000 or more (g-cata.h mol$^{-1}$), and acetic acid and/or methyl acetate is formed at a selectivity as high as about 100%. Therefore, it enables to produce acetic acid or methyl acetate industrially at a good productivity using methanol as a sole raw material.

The catalyst (A) of the present invention has a high activity, and therefore, the catalyst (A) is useful in the production of acetic acid and/or methyl acetate through a one-stage reaction starting with methanol. In particular, a solid catalyst prepared by using hydrotalcite has a high catalytic activity and a long catalytic life.

The catalyst (B) of the present invention has a high catalytic activity and can produce acetic acid and/or methyl acetate by a one-stage reaction using methanol as a sole raw material. Further, a high catalytic activity can be maintained over an extended period of time, and acetic acid and/or methyl acetate can be produced at a high selectivity.

In the present invention, the usage of a cation exchanger and an easy operation of supporting can provide the catalyst (B) having the excellent characteristics described above.

In the process of the present invention, methanol is dehydrogenated in a gas phase in the presence of a solid catalyst, which makes it possible to elevate the concentration of the catalyst. Therefore, the process of the present invention is advantageous in that the reaction rate can be enhanced. In addition, the process of the present invention is scarcely accompanied by the deposition of metals from the catalyst which has become a problem in reactions for synthesizing acetic acid or methyl acetate from methanol in a homogeneous liquid phase catalyst system. Accordingly, the catalyst is hardly deactivated even though the reaction is effected at a high temperature. In the process of the present invention, therefore, the catalytic activity can be maintained over a prolonged period of time.

In addition, when a solid catalyst comprising an Ru—Sn hetero-polynuclear compound supported on a support such as activated carbon is used in the process of the present invention, acetic acid and/or methyl acetate can be produced at a high efficiency based on the high catalytic activity of the catalyst.

When said Ru—Sn hetero-polynuclear compound is a complex represented by the above-mentioned general formula (1), the productivity of acetic acid and/or methyl acetate is further elevated on the basis of the further improved catalytic activity of said complex.

When a solid catalyst obtained through ion exchange between the anion of an anion exchanger such as hydrotalcite and the anion of an Ru—Sn hetero-polynuclear compound is used, acetic acid and/or methyl acetate can be efficiently produced on the basis of the further improved catalytic activity and the prolonged catalytic life of said solid catalyst.

When use is made the catalyst (B), acetic acid and/or methyl acetate can be produced by a one-stage reaction at high selectivity and high reaction rate using methanol as a sole raw material according to the process of the present invention. In addition, adjusting a space velocity enables to produce acetic acid and/or methyl acetate at a selectivity as high as about 100%. That is, the characteristics of the process of the present invention resides in (a) in spite of using methanol as a sole raw material, acetic acid and/or methyl acetate can be produced because of the stable and high activity of the catalyst described above, and (b) controlling a space velocity enables acetic acid and/or methyl acetate to be produced at high selectivity while maintaining high catalytic activity.

EXAMPLES

Figure 1:
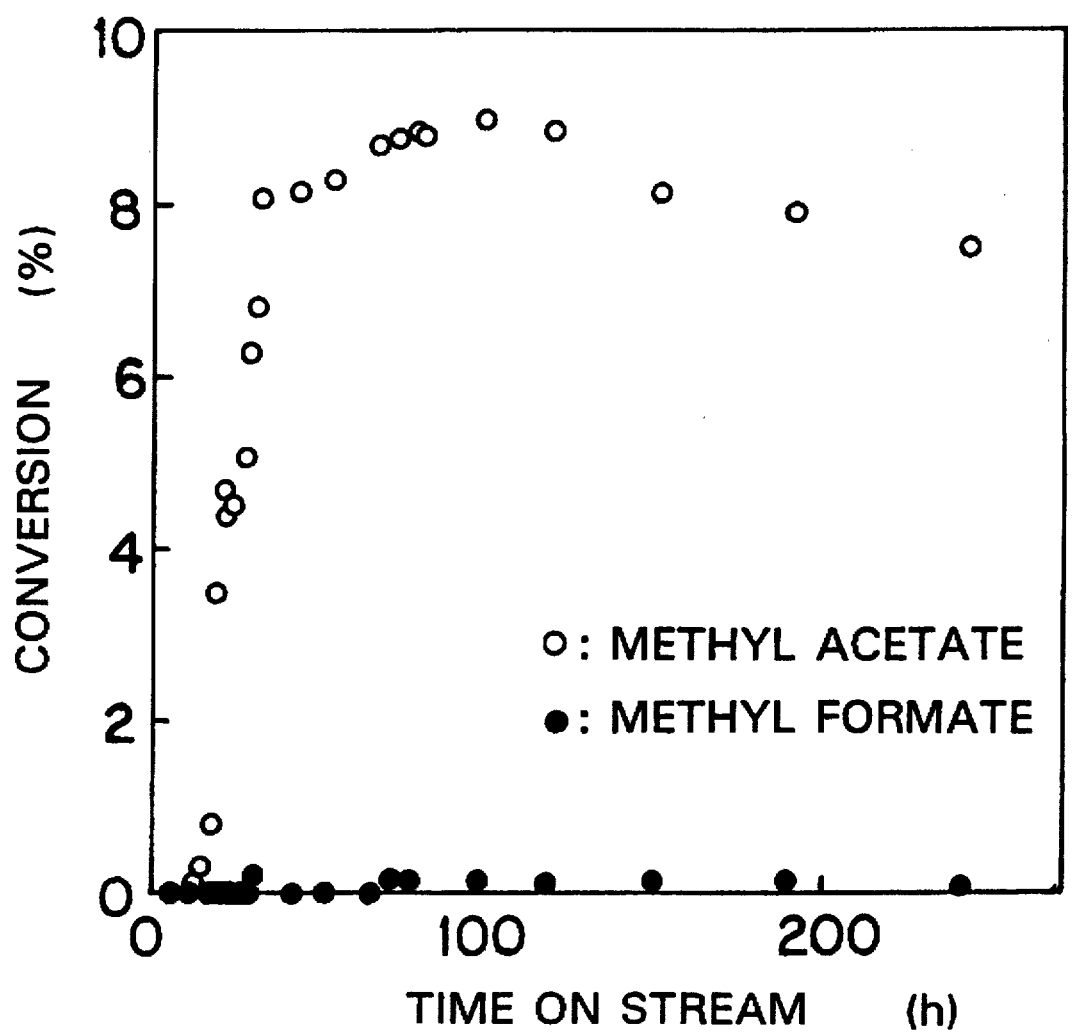
FIG. 1 is a graph showing the results in Example B-1.

Though the present invention will be described in greater detail with reference to the Examples hereinafter, it is to be understood that the scope of the present invention is not limited thereto.

In the following Examples A-1 to A-6 and Comparative Examples A-1 to A-5, acetic acid and/or methyl acetate was synthesized by using a pulse reactor and each reaction product was determined by gas chromatography, except that in Example A-6, acetic acid and/or methyl acetate were synthesized by a fixed bed flow-through system under atmospheric pressure.

Preparation 1 of complex-supporting catalyst (1) Preparation of {(Ph$_3$P)$_2$N}$_4$[Ru(SnCl$_3$)$_6$] {(Ph$_3$P)$_2$N}$_4$[Ru(SnCl$_3$)$_6$] (wherein Ph represents a phenyl group) was prepared in accordance with a method described in J. Chem. Soc., Dalton Trans., 2329 (1884).

(2) Preparation of support 722.9 parts by weight of copper nitrate (trihydrate) was dissolved in 1,500 parts by weight of water to prepare a solution A. Separately, 1253.2 parts by weight of chromium nitrate (nonahydrate) was dissolved in 7,500 parts by weight of water to prepare a solution B.

The solutions A and B were mixed together. Then 5,000 parts by weight of silica [mfd. by Kanto Chemical Co., Ltd.; silicic anhydride] was impregnated with the mixed solution thus obtained and heated at 120° to 130° C. for 1 to 3 hours to thereby remove the water and to dry. The support thus obtained was baked at 650° C. for 3 hours. Thus CuO—$Cr_2O_3$/$SiO_2$ was obtained.

(3) Preparation of complex-supporting catalyst 0.901 g of the $\{(Ph_3P)_2N\}_4[Ru(SnCl_3)_6]$ prepared in (1) was dissolved in acetonitrile to prepare 50 ml of a solution. The solution thus obtained was used to impregnate 1.0 g of the CuO—$Cr_2O_3$/$SiO_2$ prepared in (2). After drying in a vacuum at 25° C. for 15 hours, a complex-supporting catalyst was prepared.

Example A-1

0.1 g of the $\{(Ph_3P)_2N\}_4[Ru(SnCl_3)_6]$/CuO—$Cr_2O_3$/$SiO_2$, i.e., the complex-supporting catalyst prepared in "Preparation 1 of complex-supporting catalyst" (amount of the supported complex: $1.3 \times 10^{-5}$ mol) was packed in a reactor and treated by passing helium gas through the reactor at a temperature of 200° C. and at a flow rate of 25 ml/min for 3 hours.

Next, 1 µl ($2.47 \times 10^{-5}$ mol) of methanol was introduced into the reactor at a temperature of 200° C. by using helium gas as a carrier (flow rate: 25ml/min). Thus, $0.004 \times 10^{-5}$ mol of acetic acid, $0.006 \times 10^{-5}$ mol, of methyl acetate, $0.001 \times 10^{-5}$ mol of methyl formate and $0.001 \times 10^{-5}$ mol of methylal were formed.

Preparation 2 of complex-supporting catalyst (1) Preparation of $(NEt_4)_3[RuCl(SnCl_3)_5]$ $(NEt_4)_3[RuCl(SnCl_3)_5]$ (wherein Et represents an ethyl group) was prepared in accordance with a method described in J. Farrugia, et al., Can. J. Chem., 66, 1304 (1982).

(2) Preparation of $(NEt_4)_3[Ru(SnCl_3)_5(CH_3CN)]$ 1.1 g of the $(NEt_4)_3[RuCl(SnCl_3)_5]$ prepared in (1) was dissolved in acetonitrile to prepare 40 ml of a solution. To this solution was added 0.14 g of $AgBF_4$ and the precipitate thus formed was collected by filtration. The substance obtained by the filtration was washed with acetone and dried. Thus, 0.8 g (yield: 77% on the basis of Ru) of yellow powdery crystals, i.e., $(NEt_4)_3[Ru(SnCl_3)_5(CH_3CN)]$ was obtained.

(3) Preparation of complex-supporting catalyst 0.333 g of the $(NEt_4)_3[Ru(SnCl_3)_5(CH_3CN)]$ prepared in (2) was dissolved in acetone to prepare 65 ml of a solution. The obtained solution was used to impregnate 1.58 g of activated carbon [mfd. by Kansai Coke and Chemicals Co., Ltd.; Maxsorb, BET specific surface area: 3,100 m²/g] and dried in a vacuum at 25° C. for 15 hours to thereby prepare a complex-supporting catalyst.

Example A-2

0.1 g of the $(NEt_4)_3[Ru(SnCl_3)_5(CH_3CN)]$/activated carbon, i.e., the complex-supporting catalyst prepared in "Preparation 2 of complex-supporting catalyst" (amount of the supported complex: $1.05 \times 10^{-5}$ mol) was packed in a reactor and treated by passing helium gas through the reactor at a temperature of 300° C. and at a flow rate of 25 ml/min for 3 hours.

Next, 1 µl ($2.47 \times 10^{-5}$ mol) of methanol was introduced into the reactor at a temperature of 300° C. by using helium gas as a carrier (flow rate: 25 ml/min). Thus, $0.001 \times 10^{-5}$ mol of acetic acid, $0.002 \times 10^{-5}$ mol of methyl acetate, $0.043 \times 10^{-5}$ mol of methyl formate and $0.005 \times 10^{-5}$ mol of methylal were formed.

Preparation 8 of complex-supporting catalyst (1) Preparation of $(NEt_4)_4[Ru(SnCl_3)_6]$ $(NEt_4)_4[Ru(SnCl_3)_6]$ (wherein Et represents an ethyl group) was prepared in accordance with a method described in J. Chem. Soc., Dalton Trans., 2329 (1984).

Namely, in an argon gas atmosphere, 10 ml of 2M hydrochloric acid was added to a mixture of 0.5 g (1.91 mmol) of $RuCl_3 \cdot 3H_2O$ and 4.3 g (19 mmol) of $SnCl_2 \cdot 2H_2O$. The obtained mixture was stirred at 90° C. for 12 hours. During this period, the solution turned from dark brown into yellow finally. The reaction mixture was cooled to room temperature and then a solution of 1.26 g (7.6 mmol) of $NEt_4Cl$ (wherein Et represents an ethyl group) in 10 ml of 2M hydrochloric acid was dropwise added thereto to thereby form a yellow precipitate. The yellow precipitate was collected by filtration, successively washed with 2M hydrochloric acid, ethanol and diethyl ether and dried in a vacuum. Thus yellow powdery crystals were obtained (yield: 2.34 g, 62% on the basis of Ru).

(2) Preparation of support 200 g of cupric acetate, 15 g of zinc carbonate and 10 g of silica [mfd. by Kanto Chemical Co., Ltd.; silicic anhydride] were kneaded together with 80 ml of water for 3 hours. The mixture thus obtained was dried in a nitrogen gas atmosphere at 80° C. for 8 hours and then baked in a nitrogen atmosphere at 650° C. for 3 hours to thereby give a support. The resulting support comprised 80% by weight of CuO, 10% by weight of ZnO and 10% by weight of $SiO_2$.

(3) Preparation of complex-supporting catalyst 0.0986 g of the $(NEt_4)_4[Ru(SnCl_3)_6]$ prepared in (1) was dissolved in acetonitrile to prepare 10 ml of a solution. The solution thus obtained was used to impregnate 1.0 g of the support CuO—ZnO/$SiO_2$ prepared in (2). After drying in a vacuum at 25° C. for 15 hours, a complex-supporting catalyst was prepared.

Example A-3

0.1 g of the $(NEt_4)_4[Ru(SnCl_3)_6]$/CuO—ZnO/$SiO_2$, i.e., the complex-supporting catalyst prepared in "Preparation 3 of complex-supporting catalyst" (amount of the supported complex: $4.61 \times 10^{-6}$ mol) was packed in a reactor and treated by passing helium gas through the reactor at a temperature of 200° C. and at a flow rate of 25 ml/min for 3 hours.

Next, 1 µl ($2.47 \times 10^{-5}$ mol) of methanol was introduced into the reactor at a temperature of 200° C. by using helium gas as a carrier (flow rate: 25 ml/min). Thus, $0.0001 \times 10^{-5}$ mol of acetic acid, $0.003 \times 10^{-5}$ mol of methyl acetate and $0.02 \times 10^{-5}$ mol of methyl formate were formed.

Preparation 4 of complex-supporting catalyst 0.0829 g of the $(NEt_4)_3[Ru(SnCl_3)_5(CH_3CN)]$ prepared in "Preparation 2-(2) of complex-supporting catalyst" was dissolved in acetone to prepare 20 ml of a solution. The obtained solution was used to impregnate 1.0 g of the support CuO—ZnO/$SiO_2$ prepared in "Preparation 3-(2) of complex-supporting catalyst" and dried in a vacuum at 25° C. for 15 hours to thereby prepare a complex-supporting catalyst.

Example A-4

0.1 g of the $(NEt_4)_3[Ru(SnCl_3)_5(CH_3CN)]$/CuO—ZnO/$SiO_2$, i.e., the complex-supporting catalyst prepared in "Preparation 4 of complex-supporting catalyst" (amount of the supported complex: $4.64 \times 10^{-6}$ mol) was packed in a reactor and then treated in the same manner as described in Example A-3. Next, 1 μl ($2.47 \times 10^{-5}$ mol) of methanol was introduced into the reactor at a temperature of 200° C. by using helium gas as a carrier (flow rate: 25 ml/min). Thus, $0.0001 \times 10^{-5}$ mol of acetic acid, $0.0003 \times 10^{-5}$ mol of methyl acetate, $0.010 \times 10^{-5}$ mol of methyl formate and $0.0001 \times 10^{-5}$ mol of methylal were formed.

Preparation 5 of complex-supporting catalyst 0.800 g of the $(NEt_4)_4[Ru(SnCl_3)_6]$ prepared in "Preparation 3-(1) of complex-supporting catalyst" was dissolved in acetonitrile to thereby obtain 20 ml of a solution. The solution was used to impregnate 1.00 g of activated carbon [mfd. by Kansai Coke and Chemicals Co., Ltd.; Maxsorb, BET specific surface area: 3,100 $m^2/g$] and dried in a vacuum at 25° C. for 15 hours to thereby prepare a complex-supporting catalyst.

Example A-5

0.1 g of the $(NEt_4)_4[Ru(SnCl_3)_6]$/activated carbon, i.e., the complex-supporting catalyst prepared in the above "Preparation 5 of complex-supporting catalyst" (amount of the supported complex: $2.25 \times 10^{-5}$ mol) was packed in a reactor and treated by passing helium gas through the reactor at a temperature of 200° C. and at a flow rate of 25 ml/min for 3 hours.

Next, 1 μl ($2.47 \times 10^{-5}$ mol) of methanol was introduced into the reactor at a temperature of 200° C. by using helium gas as a carrier (flow rate: 25 ml/min). Thus, $5.46 \times 10^{-9}$ mol of acetic acid, $1.39 \times 10^{-8}$ mol of methyl acetate, $1.19 \times 10^{-8}$ mol of methyl formate and $6.30 \times 10^{-8}$ mol of methylal were formed.

Preparation 6 of complex-supporting catalyst (1) Preparation of hydrotalcite having intercalated terephthalate anion $[Mg_4Al_2(OH)_{12}]^{2+}(C_6H_4(COO^-)_2) \cdot zH_2O$ Hydrotalcite having an intercalated terephthalate anion was prepared in accordance with a method described in Inorg. Chem., 27, 4628 (1988). All procedures were effected in an argon atmosphere.

Namely, 13.6 of terephthalic acid and 57.5 of a 504% by weight aqueous solution of sodium hydroxide were added to 160 ml of water and the obtained mixture was heated to 60° C. and then allowed to cool to room temperature.

Then, into the solution thus obtained was dropwise added 128 ml of an aqueous solution obtained by dissolving 41.0 of $Mg(NO_3)_2 \cdot 6H_2O$ and 30.0 g of $Al(NO_3)_3 \cdot 9H_2O$ over 90 minutes under stirring. This solution was allowed to stand at 73° C. for 18 hours and the precipitate thus formed was collected by filtration and thoroughly washed with water.

The precipitate thus obtained was dried in a vacuum at 120° C. for 15 hours and ground in an agate mortar. Thus, the title compound was obtained in the form of a powder.

(2) Preparation of a catalyst having Ru—Sn heteropolynuclear compound supported on hydrotalcite All of the following procedures were effected in an argon atmosphere.

1.00 g of $RuCl_3 \cdot 3H_2O$ and 8.60 g of $SnCl_2 \cdot 2H_2O$ were dissolved in 120 ml of 2N hydrochloric acid. The obtained mixture was heated at 90° C. for 12 hours. The obtained solution was passed through an anion exchange resin (Dowex 1X-8,100–200 mesh) to thereby remove anions other than $[Ru(SnCl_3)_6]^{4-}$ therefrom.

To the solution thus obtained was added 4.00 g of $[Mg_4Al_2(OH)_{12}]^{2+}(C_6H_4(COO^-)_2) \cdot zH_2O$ prepared in (1). Ion exchange was effected by stirring the mixture at 40° C. for 12 hours. The solid matters were collected by filtration, washed with dilute hydrochloric acid and dried in a vacuum at 150° C. for 4 hours to thereby obtain a yellow powder.

The result of an analysis on the composition of the powder thus obtained by the ICP (inductively coupled plasma) spectrometry indicated Ru: Sn: Al: Mg=1: 6.5: 4.7: 7.9. Based on this result, it is considered that the obtained powder roughly has a composition $[Mg_8Al_4(OH)_{24}]^{4+}[Ru(SnCl_3)_6]^{4-} \cdot zH_2O$. Further, the result of XRD (x-ray diffractometry) indicated that the interlayer distance was 17 Å.

Example A-6

0.3 g of the catalyst obtained in the above "Preparation 6 of complex-supporting catalyst" was packed in a reactor. A mixed gas comprising 10% by mol of methanol and 90% by mol of helium was continuously supplied to the reactor at a temperature of 200° C. and at a flow rate of 6.2 ml/min. 10 minutes after the initiation of the supply of the gas, the gas produced by the reaction was analyzed. As a result, it was found out that the yields of acetic acid, methyl formate and methylal were respectively 4.2%, 3.0% and 4.6%.

Comparative Example A-1

The same experiment as that of Example A-1 was conducted except that the complex-supporting catalyst employed in Example A-1 was replaced by 0.1 g of the $CuO—Cr_2O_3/SiO_2$ which was the support employed in "Preparation 1 of complex-supporting catalyst". As a result, neither acetic acid nor methyl acetate but $0.019 \times 10^{-5}$ mol of methyl formate alone was detected as a reaction product.

Comparative Example A-2

The same experiment as that of Comparative Example A-1 was conducted except that 0.53 g of $CuO—Cr_2O_3/SiO_2$ was used. As a result, neither acetic acid nor methyl acetate but $0.011 \times 10^{-5}$ mol of methyl formate alone was detected as a reaction product.

Comparative Example A-3

The same experiment as that of Example A-1 was conducted except that the complex-supporting catalyst employed in Example A-1 was replaced by 0.1 g of the $CuO—ZnO/SiO_2$ which was the support employed in "Preparation 3 of complex-supporting catalyst". As a result, neither acetic acid nor methyl acetate but $0.037 \times 10^{-5}$ mol of methyl formate alone was detected as a reaction product.

Comparative Example A-4

The same experiment as that of Example A-1 was conducted except that the complex-supporting catalyst employed in Example A-1 was replaced by 0.1 g of the activated carbon [mfd. by Kansai Coke and Chemicals Co., Ltd.: Maxsorb, BET specific surface area: 3,100 $m^2/g$] which was the support employed in "Preparation 2 of complex-supporting catalyst". As a result, the methanol employed as the starting material was recovered at a ratio of 100%.

Comparative Example A-5

The same experiment as that of Example A-1 was conducted except that the complex-supporting catalyst employed in Example A-1 was replaced by 0.1 g of the hydrotalcite having an intercalated terephthalate anion obtained in "Preparation 6-(1) of complex-supporting catalyst". As a result, no dehydrogenation product of methanol was detected as a reaction product.

Example B-1

(1) 5.0 g of NaY type zeolite (HSZ-32ONAA, manufactured by Toso Co., Ltd., $SiO_2/Al_2O_3$=5.5, specific surface area: 700 $m^2/g$) and 0.60 g (3% by weight, as determined with respect to Ru atom, based on zeolite) of $[Ru(NH_3)_6]Cl_3$ were added to 1500 ml of an aqueous hydrochloric acid solution (pH=4.5), and stirring of the mixture thus obtained was effected in an aerial atmosphere for 48 hours, whereby zeolite which was cation-exchanged with the Ru complex was prepared.

(2) 2.23 g (Sn/Ru=25) of $SnCl_2 \cdot 2H_2O$ and 3.69 g of NaCl were dissolved in 500 ml of methanol under argon atmosphere. The zeolite (1.10 g) treated as above was added to the solution thus obtained, and after stirring the mixture thus obtained at a room temperature for 24 hours, filtration was carried out in an aerial atmosphere, followed by drying in a vacuum, whereby the catalyst was obtained.

(3) 3.0 of the above catalyst was charged in an atmospheric fixed-bed continuous flow reactor, and dried methanol was supplied together with helium as the carrier gas at the reaction temperature of 200° C. and the space velocity of 1300 (g-cata. h $mol^{-1}$) over a period of 240 hours. The reaction products were determined by gas chromatography to obtain the results shown in FIG. 1.

As apparent from FIG. 1, after the induction period of about 40 hours, the catalyst showed the activity of the conversion of about 9% for methyl acetate. Methyl acetate was formed at the selectivity of almost 100% and methyl formate was by-produced in a very little amount. Continuing the above reaction over a period of 240 hours only lowered the activity of the catalyst to some extent.

Example B-2

Figure 2:
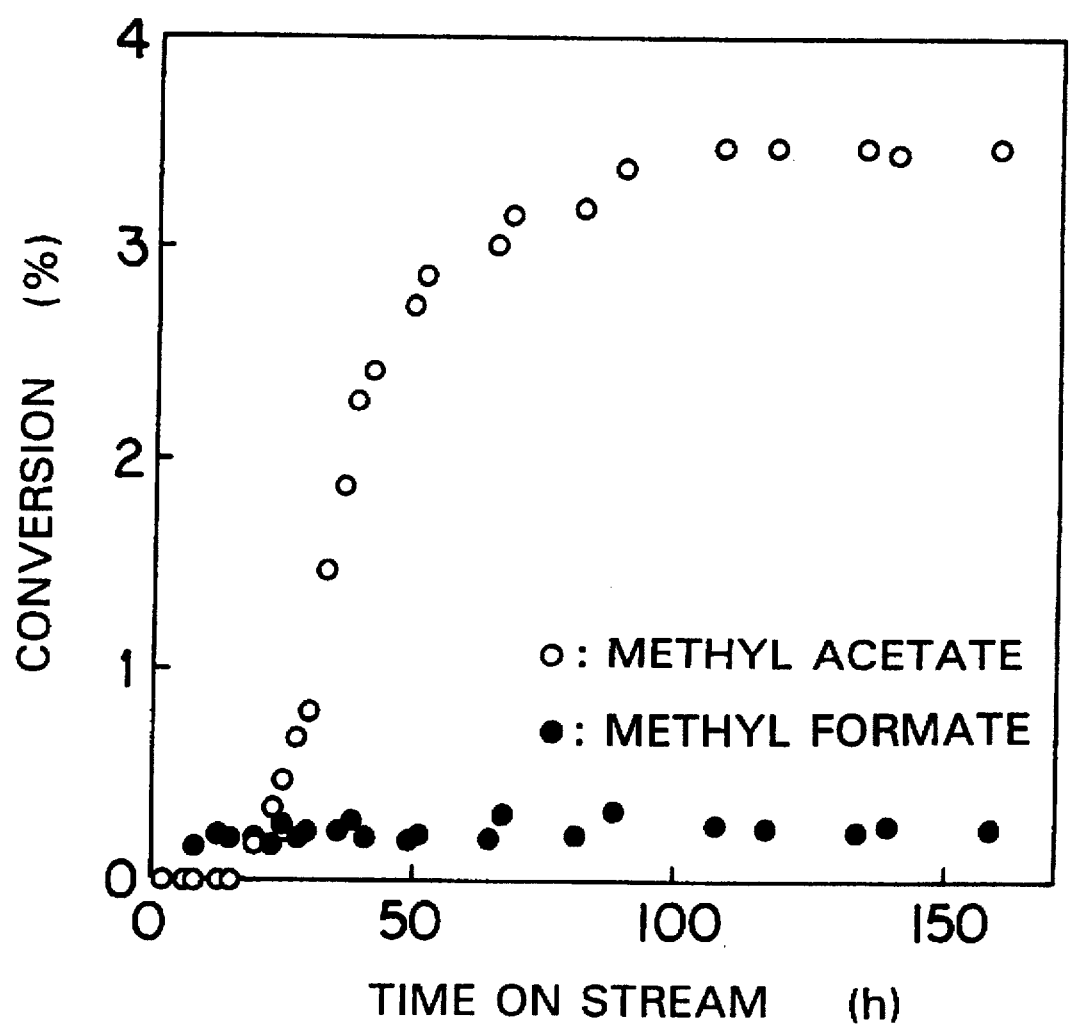
FIG. 2 is a graph showing the results in Example B-2.

1.00 g of the catalyst obtained in Example B-1 was charged in the atmospheric fixed-bed continuous flow reactor, and the reaction was carried out in the same manner as that in Example B-1, except that dried methanol was supplied together with helium as the carrier gas at the space velocity of 1100 (g-cata. h $mol^{-1}$), whereby the results shown in FIG. 2 were obtained.

As apparent from FIG. 2, after the induction period of about 70 hours, the catalyst showed the activity of the conversion of about 3.5% for methyl acetate and methyl formate was by-produced at the conversion of 0.3%. Continuing the reaction over a period of 160 hours allowed the catalyst to show the activity of the conversion of 3.5% for methyl acetate and the conversion of 0.3% for methyl formate and thus scarcely lowered the catalytic activity.

Example B-3

Figure 3:
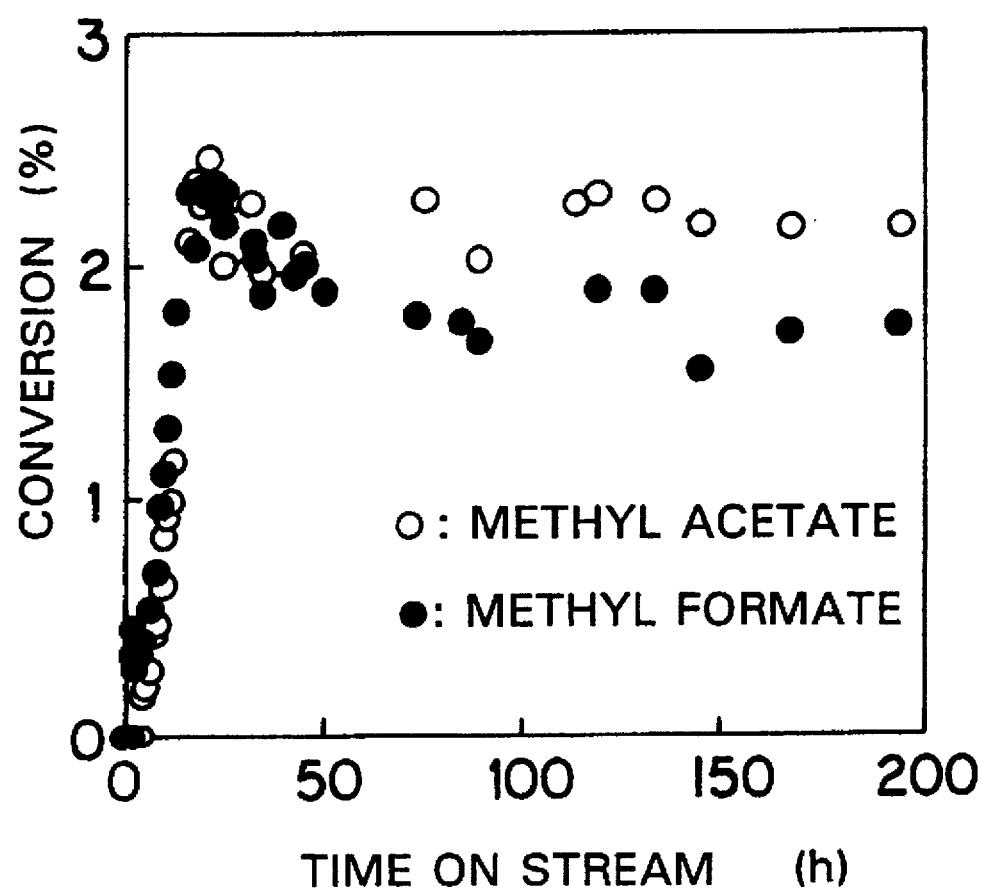
FIG. 3 is a graph showing the results in Example B-3.

300 m of the catalyst obtained in Example B-1 was charged in the atmospheric fixed-bed continuous flow reactor, and the reaction was carried out in the same manner as that in Example B-1, except that dried methanol was supplied together with helium as the carrier gas at the space velocity of 130 (g-cata. h $mol^{-1}$), whereby the results shown in FIG. 3 were obtained.

As apparent from FIG. 3, after the induction period of about 20 hours, the catalyst showed the activity of the conversion of about 2.5% for methyl acetate and methyl formate was by-produced at the conversion of 2.3%. Continuing the reaction over a period of 200 hours allowed the catalyst to show the conversion of 2.2% for methyl acetate and the conversion of 1.8% for methyl formate and scarcely lowered the catalytic activity.

As apparent from the results obtained in Examples B-1 to B-3, regulating the used amount of the catalyst and the space velocity can control the conversion for methyl acetate and methyl formate.

Comparative Example B-1

Zeolite which was subjected to a cation exchange with the Ru complex was prepared in the same manner as that in Example B-1, except that the treatment with $SnCl_2$ at the step (2) in Example B-1 was not carried out. Methanol was continuously reacted over a period of 90 hours in the same manner as that in Example B-2, except that the catalyst thus obtained was used, to find that acetic acid or methyl acetate was not formed at all while the formation of a trace amount of methyl formate was observed.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What I claim is:

1. A process for producing acetic acid and/or methyl acetate which comprises reacting methanol in the presence of a catalyst comprising a cation exchanger, a ruthenium complex which contains ruthenium of a positive valence and is supported on the cation exchanger by cation exchange and a tin compound containing divalent or tetravalent tin which also is supported on the cation exchanger.

2. The process for producing acetic acid and/or methyl acetate as claimed in claim 1, wherein methanol is reacted in a gas phase.

* * * * *